United States Patent [19]

Umezawa et al.

[11] 3,968,100

[45] July 6, 1976

[54] GUANIDIO DERIVATIVES OF KASUGAMYCIN AND THEIR PRODUCTION

[75] Inventors: Hamao Umezawa; Yasuji Suhara, both of Tokyo, Japan

[73] Assignee: Zaidan Hojin Biseibutsu Kagaku Kenkyu Kai, Tokyo, Japan

[22] Filed: Jan. 24, 1972

[21] Appl. No.: 220,374

[52] U.S. Cl.................... 260/210 AB; 260/210 R; 424/180
[51] Int. Cl.².......................................... C07H 15/22
[58] Field of Search...... 260/210 R, 210 AB, 211 R, 260/564 A

[56] References Cited
UNITED STATES PATENTS

| | | | |
|---|---|---|---|
| 3,456,009 | 7/1969 | Green et al. | 260/564 A |
| 3,647,779 | 3/1972 | Schmitz | 260/210 R |
| 3,652,535 | 3/1972 | Keil et al. | 260/210 R |

OTHER PUBLICATIONS

Suhara et al., "Chem. Abst." vol. 64, 1966, p. 15965(d).

Primary Examiner—Johnnie R. Brown
Attorney, Agent, or Firm—Brady, O'Boyle & Gates

[57] ABSTRACT

New guanidino derivatives of kasugamycin in which the oxalamidino group at the 4-position of kasugamycin molecule has been replaced by different guanidino groups are produced and found to show an improved antibacterial activity against Gram negative bacteria and a decreased toxicity to man and animals, as compared to kasugamycin itself. The new guanidino derivatives of kasugamycin may readily be produced by reacting an amine with an isourea derivative of kasugamycin which has been prepared by reacting sodium hypobromite with kasugamycin and then treating the resulting cyanamide derivative with hydrogen chloride in methanol.

5 Claims, No Drawings

GUANIDIO DERIVATIVES OF KASUGAMYCIN AND THEIR PRODUCTION

This invention relates to new and useful guanidino derivatives of kasugamycin and their production. More particularly, this invention relates to new and useful derivatives of kasugamycin in which various guanidino groups have been introduced at the 4-position of kasugamycin molecule in stead of the oxalamidino group, and this invention further relates to a process for the preparation thereof by chemical derivation of kasugamycin.

We have now succeeded in preparing new and useful guanidino derivatives of kasugamycin which may be represented by the formula:

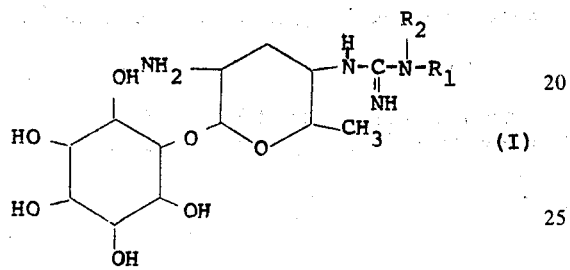

(I)

wherein $R_1$ and $R_2$ may be the same or different and are selected from hydrogen, hydroxyl, amino, an alkyl, aryl, amino-alkyl, amino-aryl and alkyl-sulfonyl, and we have found that these new guanidino derivatives of kasugamycin of the above formula (I) show an improved antimicrobial activity as compared to kasugamycin itself.

According to the present invention, therefore, there is provided a guanidino derivative of kasugamycin of the formula:

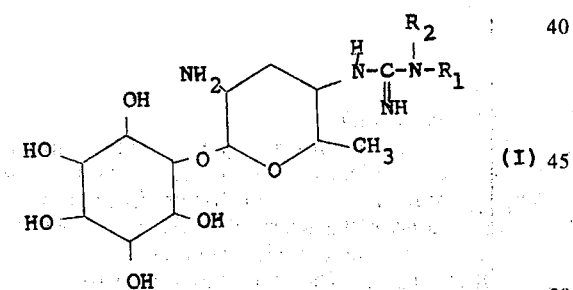

(I)

wherein $R_1$ and $R_2$ are selected from hydrogen, hydroxyl, amino, an alkyl, aryl, amino-alkyl, amino-aryl and alkyl-sulfonyl. The alkyl grop may be of 1–4 carbon atoms. The aryl group may be, for example, phenyl.

According to a preferred embodiment of the present invention, there is provided a guanidino derivative of kasugamycin of the formula:

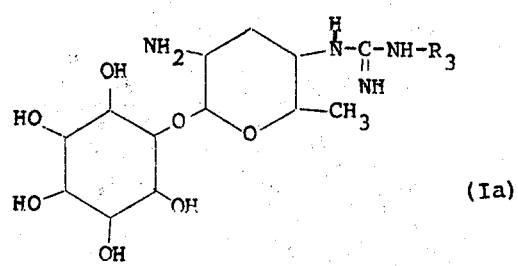

(Ia)

wherein $R_3$ is aminoethyl, aminopropyl or aminobutyl, and it has been found that a guanidino derivative of kasugamycin of the formula (Ia) exhibits an antimicrobial activity of 50–100 folds higher than that of kasugamycin itself. As the derivative of the formula (Ia) there may specifically be mentioned the following compounds:

A. 1D-3-O-{2-amino-4-[(2-aminoethyl)-guanidino]-2,3,4,6-tetradeoxy-α-D-arabino-hexopyranosyl}-chiro-inositol.

1D-3-O-{ 2-amino-4-[(2-aminopropyl)-guanidino]-2,3,4,6-tetradeoxy-α-D-arabino-hexopyranosyl}-chiro-inositol.

1D-3-O-{2-amino-4-[(2-aminobutyl)-guanidino]-2,3,4,6-tetradeoxy-α-D-arabino-hexopyranosyl}-chiro-inositol.

The guanidino derivative of kasugamycin of the formula (I) may be prepared by oxidative decarboxylation of kasugamycin with sodium hypobromite to a cyanamide derivative followed by treatment with hydrogen chloride in methanol to an isourea derivative and by reaction with various amines to the guanidino derivatives of kasugamycin.

The preparation of the new guanidino derivative of kasugamycin may be illustrated by the following schema:

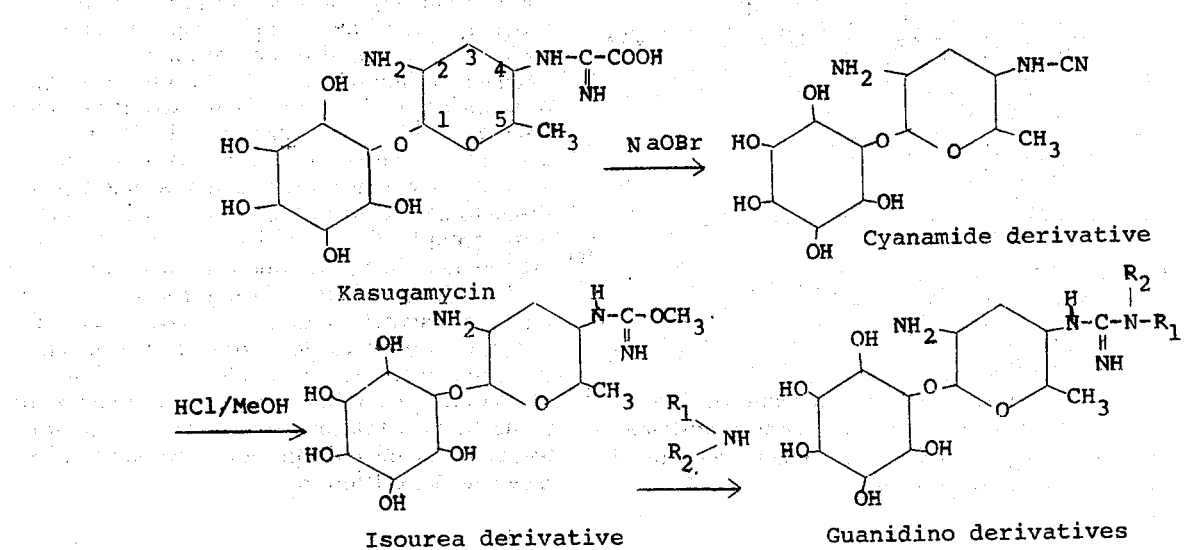

According to another aspect of the present invention, therefore, there is provided a process for the preparation of a guanidino derivative of kasugamycin of the formula:

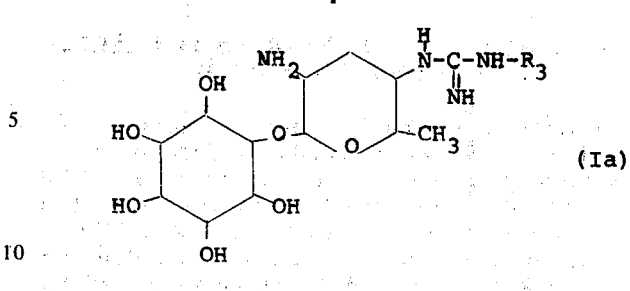

(Ia)

wherein $R_3$ is aminoethyl, aminopropyl or aminobutyl, which comprises reacting an amine of the formula:

$$H_2N-(CH_2)_n-NH_2 \qquad (IIa)$$

wherein $n$ is an integer of 2, 3, and 4, with an isourea derivative of kasugamycin of the formula:

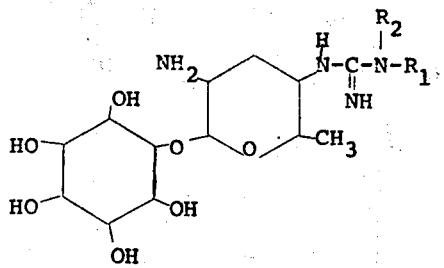

(I)

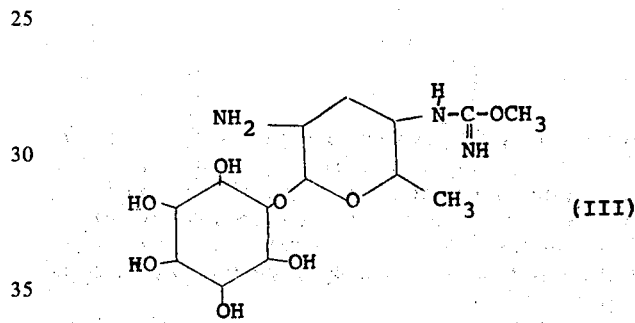

(III)

wherein $R_1$ and $R_2$ are selected from hydrogen, hydroxyl, amino, an alkyl, aryl, amino-alkyl, amino-aryl and alkyl-sulfonyl, which comprises reacting an amine of the formula:

$$R_1-NH-R_2 \qquad (II)$$

wherein $R_1$ and $R_2$ are as defined above, with an isourea derivative of kasugamycin of the formula:

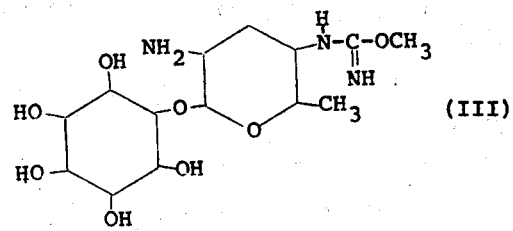

(III)

in a known manner. According to a limited form of this aspect of the present invention, there is provided a process for the preparation of a guanidino derivative of kasugamycin of the formula:

in a known manner.

The process according to the present invention may be effected in a known manner, for example, by reacting an amine of the formula (II) or (IIa) with the isourea derivative of kasugamycin (III) in an inert organic solvent such as methanol, ethanol with or without application of heat. The guanidino derivative of kasugamycin (I) or (Ia) so formed may be recovered from the reaction mixture, for example, by precipitation, and it may then be purified by treating with a cation-exchange resin such as Amberlite IRC-50(H-type) (a registered trade name of a weakly acidic cation-exchange resin which is produced by Rohm & Haas Co., U.S.A. and which is composed of a methacrylic acid-divinylbenzene copolymer having macro-reticular structure and containing carboxyl groups as the functional group). The guanidino derivative absorbed on the cation-exchange resin may be eluted with an acid such as diluted sulfuric acid or hydrochloric acid, after the resin has been washed with water and aqueous ammonia to remove the un-reacted amine compound. Results of elementary analysis for some ganidino derivatives of kasugamycin which were prepared according to the process of the present invention and purified by the above-mentioned procedure of purification are shown in Table 1 below.

TABLE 1

| Compound No. | | | C% | H% | N% |
|---|---|---|---|---|---|
| 1 | $R_1=(CH_2)_2NH_2$ | Calcd. | 45.82 | 7.89 | 17.80 |
| | $R_2=H$ | Found | 45.53 | 7.80 | 17.45 |
| 2 | $R_1=(CH_2)_2N(CH_3)_2$ | Calcd. | 48.48 | 8.31 | 16.62 |
| | $R_2=H$ | Found | 48.15 | 8.19 | 16.25 |
| 3 | $R_1=(CH_2)_2NHCH_3$ | Calcd. | 48.48 | 8.31 | 16.62 |
| | $R_2=CH_3$ | Found | 48.88 | 8.11 | 16.23 |
| 4 | $R_1=(CH_2)_4NH_2$ | Calcd. | 48.48 | 8.31 | 16.62 |
| | $R_2=H$ | Found | 48.09 | 8.20 | 16.19 |
| 5 | $R_1=(CH_2)_3NHCH_3$ | Calcd. | 47.20 | 8.10 | 17.19 |
| | $R_2=H$ | Found | 46.86 | 8.32 | 16.85 |
| 6 | $R_1=CH_2CH(NH_2)CH_3$ | Calcd. | 47.20 | 8.10 | 17.19 |
| | $R_2=H$ | Found | 47.56 | 8.32 | 16.84 |
| 7 | $R_1=R_2=$ —C$_6$H$_4$—OCH$_3$ | Calcd. | 57.67 | 6.76 | 9.96 |
| | $R_2=H$ | Found | 57.29 | 6.38 | 9.46 |
| 8 | $R_1=CH_2 \cdot CH_2SO_3H$ | Calcd. | 39.31 | 6.55 | 12.22 |
| | $R_2=H$ | Found | 39.03 | 6.43 | 11.88 |
| 9 | $R_1=NH$—C$_6$H$_5$ | Calcd. | 51.72 | 7.03 | 15.87 |
| | $R_2=H$ | Found | 52.00 | 7.24 | 15.67 |
| 10 | $R_1=NH_2$ | Calcd. | 42.76 | 7.40 | 19.17 |
| | $R_2=H$ | Found | 42.41 | 7.38 | 18.90 |
| 11 | $R_1=OH$ | Calcd. | 42.64 | 7.10 | 15.30 |
| | $R_2=H$ | Found | 42.32 | 7.03 | 15.01 |

The new guanidino derivatives of kasugamycin according to the present invention are more highly active against Gram negative bacteria, much more easily soluble in water and less toxic to man and animals than kasugamycin itself. The antibacterial spectrum of the new guanidino derivatives of kasugamycin was determined by the broth dilution method and shown in Table 2 below.

General characteristics of the new guanidino derivatives of kasugamycin are that they are more active against Gram positive and negative bacteria, more stable at alkaline conditions and exhibiting weaker toxicity than kasugamycin. The new kasugamycin derivatives, therefore, are useful as chemotherapeutic agents for human and animals, and as growth promoting substances for animals.

TABLE 2

| | Minimum inhibitory concentration (mcg/ml) Compound of the formula (I) | | | | | |
|---|---|---|---|---|---|---|
| Test organisms | $R_1=$ —$(CH_2)_2NH_2$, $R_2=H$ | $R_1=$ —$(CH_2)_3NH_2$, $R_2=H$ | $R_1=$ $(CH_2)_4NH_2$, $R_2=H$ | $R_1=$ —$(CH_2)_2NHCH_3$, $R_2=CH_3$ | $R_1=$ —$(CH_2)_2SO_3H$, $R_2=H$ | Kasugamycin |
| Staphylococcus aureus 6538P | 0.78 | — | 0.2 | 50 | 12.5 | 50 |
| Bacillus subtilis ATCC 6633 | 0.39 | — | 0.78 | 25 | 100 | >100 |
| Escherichia coli NIHJ | 0.78 | 0.39 | 12.5 | 100 | >100 | 100 |
| Escherichia coli K-12 | 0.39 | — | 1.56 | 100 | >100 | 100 |
| Klebsiella pneumoniae ATCC 10031 | 0.1 | 0.2 | 1.56 | 100 | >100 | 50 |
| Proteus vulgaris OX 19 | 0.78 | — | 1.56 | 50 | >100 | 100 |
| Pseudomonas aeruginosa A$_3$ | 0.39 | 0.39 | 1.58 | 50 | 100 | 100 |
| Pseudomonas fluorescence NIHJB-24 | 1.56 | — | 3.13 | 50 | 50 | 3.13 |
| Salmonella paratyphi A | 0.2 | — | 0.78 | 50 | 50 | 50 |
| Shigella sonnei 191-66 | 1.56 | — | 6.25 | 100 | >100 | >100 |

Among the guanidino derivatives of kasugamycin according to the present invention, one of the most active derivative ($R_1=CH_2CH_2NH_2$, $R_2=H$) which is now designated kasugamycin-KG-8 was tested for its effect in vivo against *Pseudomonas aeruginosa*. The curative dose ($CD_{50}$) of kasugamycin-KG-8 was 3.13 mg/kg, while that of kasugamycin itself tested at the same experimental condition was 35.5 mg/kg. It is expected, therefore, that the new guanidino derivatives are useful chemotherapeutic agents for pseudomonas infections. The new guanidino derivative of kasugamycin according to the present invention may conventionally be formulated into tablet or capsule for oral administration and into aqueous solution or suspension for injection, with or without pharmaceutically acceptable additive such as carrier, vehicle, suspension agent and others. It may be used in the form of an acid-addition salt for administration.

The new guanidino derivatives of kasugamycin, especially kasugamycin-KG-8 is useful and effective in promoting the growth of animals. It can be supplied to all poultries and stock or domestic animals which comprises chicken, turkey, pig, sheep and cattle. Addition of kasugamycin-KG-8 is adequate in a proportion of 0.001 to 0.1% in a feed or drinking water which is fed to poultry or stock animals. It is also possible to supply kasugamycin-KG-8 to the animals directly as such or in admixture with appropriate diluent.

According to a third aspect of the present invention, therefore, there is provided a process of promoting the growth of poultry and stock animals which comprises supplying an effective amount of the new guanidino derivatives of kasugamycin to them.

The present invention is now illustrated with reference to Examples. However, Examples are merely illustrative and it should be understood that the present invention is not limited thereto.

EXAMPLE 1

Preparation of cyanamide derivative of kasugamycin.

To a stirred solution containing 10 g of kasugamycin hydrochloride in 140 ml of water at room temperature, a bromine solution in methanol (4.99 g of bromine in 16 ml of methanol) and 1N sodium hydroxide were alternatively added keeping at pH 5 – 6 for 1 hour. After the addition of the bromine solution, the reaction mixture was stirred for 30 minutes and allowed to stand in cold over-night. The mixture was diluted with 900 ml of water and poured into a column containing 1000 ml of cation exchange resin Dowex 50W, X4 (50 – 100 meshes, $NH_4^+$ type) at a flow rate of 2 ml per minutes. The column was washed with water and developed with 0.2N aqueous ammonia, and the eluate was fractionated in 15 ml portion. Fraction No. 40 - 85, which gave positive ninhydrin test were collected, concentrated under reduced pressure, adjusted to pH 4 with 1N hydrochloric acid, and lyophylized to yield 8.0 g of the cyanamide derivative hydrochloride as a white powder. Yield was 93%. The free base of the derivative was crystallized from water. The crystals melted at 72° – 74°C, bubbled at 160° – 163°C, and turned brown gradually above 240°C. $[\alpha]_D^{20} = +118°$ (c, 0.5 in $H_2O$). The infrared spectrum (KBr pellet) shows a strong band at 2220 $mc^{-1}$ attributed to nitril group.

Anal. Calcd. for $C_{13}H_{23}O_7N_3$: C, 46.84; H, 6.96; N, 12.61. Found: C, 46.75; H, 6.88; N, 13.01.

EXAMPLE 2

Preparation of isourea derivative of kasugamycin.

A solution containing 2.715 g of cyanamide derivative hydrochloride of kasugamycin, which was prepared in Example 1, in 0.5N methanolic hydrogen chloride was allowed to stand at room temperature for 48 hours. To the solution was added 140 ml of anhydrous ethyl ether to give white precipitate. By filtration and washing with ethyl ether, 3.241 g of isourea derivative dihydrochloride of kasugamycin was yielded in the form of white powder.

EXAMPLE 3

Preparation of a guanidino derivative of kasugamycin of the formula (I) where $R_1$ is $-CH_2CH_2NH_2$ and $R_2$ is hydrogen.

The isourea derivative dihydrochloride of kasugamycin (500 mg) prepared in Example 2 was dissolved into 10% ethylenediamine in methanol (w/w). The solution was allowed to stand at room temperature for 24 hours, diluted with 80 ml of isopropanol and concentrated to one-half volume under reduced pressure. The solid deposited by concentration was filtered, washed with ethyl ether and dried to give 457 mg of a crude guanidino derivative of kasugamycin as a white powder. The crude powder was dissolved in 4.5 ml of water and adsorbed on a column containing 12 ml of a cation-exchange resin Amberlite IRC-50($NH_4$-type). The column was washed with water and followed with 0.3N $NH_4OH$, and developed with 0.3N $H_2SO_4$. The activities of each eluted fraction were determined using *Pseudomonas fluorescens* NIHJ B-254 as a test organism. The active fraction combined was desalted with an anion-exchange resin Amberlite IR-400(OH-type) and liophylized yielding 350 mg of white powder, which showed three times active than kasugamycin against the aforementioned test organism. The product shows a single spot on high voltage paper electrophoresis (3500 V, 15 minutes), developing with formic acid:acetic acid:water = 22:75:900. And the product formed crystals as the salt of p-hydroxyazobenzene-p′-sulfonic acid.

Anal. Calcd. for $C_{39}H_{51}O_{15}N_9S_2 \cdot 2H_2O$: C, 47.52; H, 5.58; N, 12.78. Found: C, 48.23; H, 5.36; N, 12.41.

From this dye salt there was liberated the free base, namely {1D-3-O- 2-amino-4-[(2-aminoethyl)-guanidino]-2,3,4,6-tetradeoxy-α-D-arabino-hexopyranosyl}-chiro-inositol. This compound is soluble in water, dimethylformamide and low alcohols, but scarcely soluble or insoluble in other organic solvents. It shows $[\alpha]_D + 119.7°$ (c=1, $H_2O$).

Anal. Calcd. for $C_{15}H_{31}O_7N_5$: C, 45.82; H, 7.89; N, 17.80. Found: C, 45.53; H, 7.80; N, 17.45.

Acute toxicity ($LD_{50}$) to mice injected intravenously was 380 mg/kg.

EXAMPLES 4–5

The process of Example 3 was repeated using propylenediamine and butylenediamine, respectively in stead of the ethylenediamine. There were obtained 1D-3-O-{2-amino-4-[(2-aminopropyl)-guanidinol]-2,3,4,6-tetradeoxy-α-D-arabino-hexopyranosyl}-chiro-inositol and {1D-3-O- 2-amino-4-[(2-aminobutyl)-guanidinol]-2,3,4,6-tetradeoxy-α-D-arabino-hexopyranosyl}-chiro-inositol in yields of 31.2% and 24.6%, respectively. The former compound shows $[\alpha]_D^{27}+93°$ (c=1, H$_2$O) and the latter compounds shows $[\alpha9_D^{27}+101.9°$ (c=0.6, H$_2$O). When the former compound was intraveneously injected to five mice at a dosage of 350 mg/kg, none of them was dead. When the latter compound was intraveneously injected to five mice at the same dosages, one of them was dead.

EXAMPLE 6

The result of the protection test against infection in mice of Pseudomonas aeruginosa No. 12 is indicated in Table 3. The inoculum size of *Pesudomonas aeruginosa No.*12, which was 10 times of LD$_{50}$ (3.1 × 10$^8$ cells/ml, 0.25 ml/mouse), was inoculated intraperitoneally to dd strain of mice (19–21 g body weight), and the treatment with the aforesaid kasugamycin-KG-8 was intraperitoneally injected at 0 and 6 hours after the infection. The CD$_{50}$ of this guanidino derivative was 3.13 mg/kg, while that of kasugamycin tested at the same experimental conditions was 35.5 mg/kg.

TABLE 3

| Dose at one time (mg/mouse) | Number survived/Number infected Days after infection | | | | | | |
|---|---|---|---|---|---|---|---|
| | 0 | 1 | 2 | 3 | 4 | 5 | 6 | 7 |
| 2.0 | 0/4 | | | | | | | 0/4 |
| 1.0 | 0/4 | | | | | | | 0/4 |
| 0.5 | 0/4 | | | | | | | 0/4 |
| 0.25 | 0/4 | | | | | | | 0/4 |
| 0.125 | 0/4 | | | | 1/4 | | | 1/4 |
| 0.063 | 0/4 | 1/4 | 2/4 | | | | | 2/4 |
| 0.031 | 0/4 | 4/4 | | | | | | 4/4 |
| Untreated | 0/10 | 10/10 | | | | | | 10/10 |

EXAMPLE 7

Growth promoting effect of kasugamycin-KG-8 on swine is described below.

Kasugamycin-KG-8 was mixed uniformly with ration and administered to pigs to examine its effect on growth promotion and improvement of feed utilization.

Fourty-eight young pigs of 1 month old were assigned to two lots of 29 pigs each and fed for 7 weeks.

Lot 1 (Control): Supplied only with basal ration.

Lot 2: Supplied with basal ration + kasugamycin-KG-8 10 g/ton.

As the basal ration, one of standard composition was used. Swine raising was managed according to usual method. Each lot of 29 pigs were fed in a concrete pen. Ration and drinking water were supplied ad libitum.

Results for weight gain and feed conversion are shown in Table 4. The index of weight gain indicates beneficial effect of kasugamycin-KG-8 on swing growth promotion.

TABLE 4

| | Lot 1 (control) | Lot 2 (tested) |
|---|---|---|
| Weight gain (kg) | 8.20 | 9.09 |
| Index | 100 | 110.9 |
| Feed conversion | 3.05 | 2.94 |

EXAMPLE 8

Growth promoting effect of kasugamycin-KG-8 on chicks is tested below.

Kasugamycin-KG-8 was mixed uniformly with ration and administered to chicks to examine its effect on growth promotion and improvement of feed utilization.

Eighty chicks of broiler type (White Rock × White Cornish) were assigned to two lots of 40 chicks each and for 8 weeks.

Lot 1 (Control): Supplied only with basal ration.

Lot 2: Supplied with basal ration + kasugamycin-KG-8 10 g/ton.

As the basal ration was used one of standard composition. Chick rearing was managed according to the usual method. Ration and drinking water were supplied ad libitum.

Results for weight gain and feed conversion are shown in Table 5 and 6, respectively. Tabel 5 indicates beneficial effect of kasugamycin-KG-8 on chick growth promotion.

TABLE 5

| | Lot 1 | Lot 2 |
|---|---|---|
| Starter period of 4 weeks | | |
| Weight gain (kg) | 458.4 | 496.2 |
| Index | 100 | 108.2 |
| Grower period for 4 weeks | | |
| Weight gain (kg) | 871.8 | 957.8 |
| Index | 100 | 109.9 |
| Total period through 8 weeks | | |
| Weight gain (kg) | 1330.2 | 1454.0 |
| Index | 100 | 109.3 |

TABLE 6

| | Lot 1 | Lot 2 |
|---|---|---|
| Starter period | 2.15 | 2.15 |
| Grower period | 3.65 | 3.56 |
| Total period | 3.12 | 3.07 |

What we claim is:

1. A guanidino derivative of kasugamycin of the formula:

(I)

wherein R$_1$ and R$_2$ are hydrogen, hydroxyl, amino, alkyl, amino-alkyl, phenyl, or alkyl-sulfonyl, wherein said alkyl, amino-alkyl and alkyl-sulfonyl group have 1–4 carbon atoms.

2. A guanidino derivative of kasugamycin of the formula:

(Ia)

wherein $R_3$ is aminoethyl, aminopropyl or aminobutyl.

3. 1D-3-O-{2-amino-4-[(2-aminoethyl)-guanidino]-2,3,4,6-tetradeoxy-α-D-arabino-hexopyranosyl}-chiro-inositol.

4. 1D-3-O-{2-amino-4-[(2-aminopropyl)-guanidino]-2,3,4,6-tetradeoxy-α-D-arabino-hexopyranosyl}-chiro-inositol.

5. 1D-3-O-{2-amino-4-[(2-aminobutyl)-guanidino]-2,3,4,6-tetradeoxy-α-arabino-hexopyranosyl}-chiro-inositol.

* * * * *